United States Patent
Hendriks et al.

(10) Patent No.: US 9,757,201 B2
(45) Date of Patent: Sep. 12, 2017

(54) ENERGY APPLICATION PLANNING APPARATUS

(75) Inventors: Bernardus Hendrikus Wilhelmus Hendriks, Eindhoven (NL); Nicolaas Jan Noordhoek, Best (NL); Gerhardus Wilhelmus Lucassen, Eindhoven (NL); Pieter Maria Mielekamp, Veldhoven (NL); Rami Nachabé, Eindhoven (NL); Marjolein Van Der Voort, Valkenswaard (NL); Waltherus Cornelis Jozef Bierhoff, Veldhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 246 days.

(21) Appl. No.: 14/131,518

(22) PCT Filed: Jul. 5, 2012

(86) PCT No.: PCT/IB2012/053427
§ 371 (c)(1),
(2), (4) Date: Jan. 8, 2014

(87) PCT Pub. No.: WO2013/008148
PCT Pub. Date: Jan. 17, 2013

(65) Prior Publication Data
US 2014/0142563 A1 May 22, 2014

Related U.S. Application Data

(60) Provisional application No. 61/506,328, filed on Jul. 11, 2011.

(51) Int. Cl.
*A61B 18/04* (2006.01)
*A61B 19/00* (2006.01)
(Continued)

(52) U.S. Cl.
CPC .............. *A61B 19/50* (2013.01); *A61B 18/14* (2013.01); *A61B 34/10* (2016.02); *A61B 2018/00577* (2013.01); *A61B 2034/101* (2016.02)

(58) Field of Classification Search
CPC ................... A61B 18/14; A61B 19/50; A61B 2018/00577; A61B 2019/501–2019/507
See application file for complete search history.

(56) References Cited

U.S. PATENT DOCUMENTS 5,385,544 A * 1/1995 Edwards ................ A61B 18/00
604/164.08
5,470,350 A * 11/1995 Buchholtz ............ A61B 8/0833
600/435

(Continued)

FOREIGN PATENT DOCUMENTS

JP 2001037775 A 2/2001
JP 2009160013 A 7/2009
(Continued)

OTHER PUBLICATIONS

L. Mundeleer et al., Computer-Assisted Needle Positioning for Liver Tumour Radiofrequency Ablation (RFA), IJMRCAS, 5(4), pp. 458-464, Dec. 2009.

(Continued)

*Primary Examiner* — Daniel Fowler

(57) ABSTRACT

The invention relates to an energy application planning apparatus for planning an application of energy to an object (3) like a tumor. An energy application element representation represents an energy application element (5) like an ablation needle including an energy application part for applying energy and a sensing part (7). An arrangement of the energy application element (5) with respect to the object (3) is determined depending on the positions of the energy application part and the sensing part (7) with respect to the (Continued)

energy application element (5) as defined by the energy application element representation and depending on the object representation. The application of energy can therefore not only be planned such that the application of energy is performed as desired, but also such that the object and/or a surrounding of the object are sensible as desired. In this way, the planning procedure can be improved.

13 Claims, 9 Drawing Sheets

(51) Int. Cl.
*A61B 18/14* (2006.01)
*A61B 18/00* (2006.01)
*A61B 34/10* (2016.01)

(56) References Cited

U.S. PATENT DOCUMENTS

| | | | |
|---|---|---|---|
| 6,015,390 A * | 1/2000 | Krag | A61B 18/02 128/DIG. 27 |
| 6,241,725 B1 | 6/2001 | Cosman | |
| 6,575,969 B1 * | 6/2003 | Rittman, III | A61B 18/1482 128/898 |
| 8,267,927 B2 | 9/2012 | Dalal et al. | |
| 8,417,491 B2 | 4/2013 | Trovato et al. | |
| 2003/0069577 A1 | 4/2003 | Vaska et al. | |
| 2003/0130711 A1 * | 7/2003 | Pearson | A61B 18/1477 607/101 |
| 2006/0229515 A1 | 10/2006 | Sharareh et al. | |
| 2007/0066968 A1 * | 3/2007 | Rahn | A61B 5/01 606/27 |
| 2008/0221650 A1 | 9/2008 | Turner et al. | |
| 2010/0030098 A1 * | 2/2010 | Fojtik | A61B 5/015 600/549 |
| 2010/0063496 A1 | 3/2010 | Trovato et al. | |
| 2010/0331782 A1 | 12/2010 | Hendriks et al. | |

FOREIGN PATENT DOCUMENTS

| | | |
|---|---|---|
| WO | WO2008003642 | 1/2008 |
| WO | WO2010064154 | 6/2010 |
| WO | WO2011025640 | 3/2011 |
| WO | WO2011070476 | 6/2011 |

OTHER PUBLICATIONS

Nachabe, R. et al., "Estimation of lipid and water concentrations in scattering media with diffuse optical spectroscopy from 900 to 1600 nm", Journal of Biomedical Optics, My 2010.

Nachabe, R. et al., "Effect of bile absorption coefficients on the estimation of liver tissue optical properties and related implications in", Biomedical Optics Express, Mar. 2011.

* cited by examiner

ENERGY APPLICATION PLANNING APPARATUS

CROSS-REFERENCE TO PRIOR APPLICATIONS

This application is the U.S. National Phase application under 35 U.S.C. §371 of International Application Serial No. PCT/IB2012/053427, filed on Jul. 5, 2012, which claims the benefit of Provisional U.S. Application Ser. No. 61/506,328, filed on Jul. 11, 2011. These applications are hereby incorporated by reference herein.

FIELD OF THE INVENTION

The invention relates to an energy application planning apparatus, an energy application planning method and an energy application planning computer program for planning an application of energy to an object.

BACKGROUND OF THE INVENTION

US 2011/0015628 A1 discloses an apparatus for planning an ablation procedure to eliminate a tissue mass in a patient. A tissue mass is identified in the patient, and an image representation of an initial planned target volume encompassing the tissue mass is generated. The initial planned target volume is inscribed in a template ellipsoidal enclosing ablation volume. Minor axes of the template ellipsoidal enclosing ablation volume and the initial planned target volume are scaled upward until they are equal in magnitude to a major axis of the template ellipsoidal enclosing ablation volume, to generate an enclosing sphere that encompasses the scaled planned target volume. In a lookup table a pre-computed ablation solution having a minimum number of spherical ablation regions that cover the enclosing sphere is identified, and a graphical representation of the identified pre-computed ablation solution overlaid on the sphere is output to a user.

SUMMARY OF THE INVENTION

It is an object of the present invention to provide an energy application planning apparatus, an energy application planning method and an energy application planning computer program for planning an application of energy to an object, wherein the planning of the application of energy can be improved.

In a first aspect of the present invention an energy application planning apparatus for planning an application of energy to an object is presented, wherein the energy application planning apparatus comprises:

an object providing unit for providing an object representation of the object, an energy application element providing unit for providing an energy application element representation representing an energy application element including an energy application part for applying energy to the object and a sensing part for generating a sensing signal being indicative of a property of at least one of the object and the surrounding of the object, an arrangement determination unit for determining an arrangement of the energy application element with respect to the object depending on the positions of the energy application part and the sensing part with respect to the energy application element as defined by the energy application element representation and depending on the object representation.

Since the arrangement determination unit is adapted to determine the arrangement of the energy application element with respect to the object not only depending on the position of the energy application part with respect to the energy application element, but also depending on the position of the sensing part with respect to the energy application element, the position of the sensing part with respect to the object can be considered, while planning the application of energy. This allows planning the application of energy such that not only the application of energy is performed as desired, but also such that the object and/or a surrounding of the object are sensible as desired. In this way, the planning procedure can be improved.

The object is preferentially a tumor and the energy application element is preferentially an ablation needle for ablating the tumor. In particular, the energy application part can comprise an ablation electrode surrounded by several sensing parts, which preferentially comprise optical sensors for optically sensing a property of at least one of the object and the surrounding of the object. The ablation electrode is preferentially a radio frequency (RF) ablation electrode. The sensing parts can be used for monitoring the development of an ablated region, while the needle is located within the tumor in the planned arrangement and while the energy is applied by the ablation electrode.

The arrangement determination unit can be adapted to determine one or several arrangements of the energy application element with respect to the object for applying energy to the object one or several times.

The object providing unit can be adapted to segment the object in a three-dimensional image like a computed tomography image or a magnetic resonance image for providing the object representation. The object providing unit can also be a storing unit in which the object representation, for example, a segmented tumor, is stored already, or an entire system comprising an imaging modality for generating a three-dimensional image showing the object and a segmentation unit for segmenting the object in the generated three-dimensional image.

The energy application element providing unit is preferentially a storing unit in which the energy application element representation is stored and from which the energy application element representation can be retrieved for determining the arrangement of the energy application element with respect to the object.

The object is preferentially a tumor and the sensing part is preferentially adapted to determine whether the respective tumor region of the object sensed by the respective sensing part has been ablated or not. In particular, one or several sensing parts are provided comprising optical sensors for optically sensing the tissue at the respective sensing part, wherein it can be determined whether the tissue is ablated or not based on the optical sensing.

In a preferred embodiment, the arrangement determination unit is adapted to determine the position and the orientation of the energy application element with respect to the object as the arrangement.

It is preferred that the energy application planning apparatus comprises an energy influence assignment providing unit for providing assignments between expected energy influence zones, which define an expected shape and an expected size of a zone of the object being influenced by the application of energy, and further energy application parameters, wherein the arrangement determination unit is adapted to determine the position of the energy application element by determining the position of the energy application part and a further energy application parameter depending on the object representation and the provided assignments. The further energy application parameter is, for example, the power applied to the energy application part, the time of applying energy, et cetera.

The object is preferentially a part of a living being, wherein the energy application planning apparatus can be adapted to plan an ablation of tissue of the object by the application of energy, wherein the energy influence zone is an expected ablation zone, which defines the expected shape and the expected size of an ablated zone of the living being.

It is further preferred that the arrangement determination unit is adapted to determine the position of the energy application element by determining a position of the energy application part and by determining a further energy application parameter such that the object representation is completely covered by the energy influence zone defined by the provided assignments, the position of the energy application part and the further energy application parameter. This allows determining the position of the energy application part, in particular, of an ablation RF electrode, such that the object, for instance, a tumor, is completely ablated.

It is also preferred that the arrangement determination unit is adapted to determine the orientation of the energy application element such that a provided safety margin surrounding the object representation is sensible by the sensing part. Thus, during applying the energy to the object and/or after the energy has been applied to the object, while the energy application element is arranged in the determined arrangement within the object, it can be sensed by the sensing part of the energy application element, whether the influence of the application of energy has reached the safety margin, whereby it can be concluded whether the object has been influenced completely, for example, has been ablated completely, at least between the position of the energy application part and the part of the safety margin sensed by the sensing part or not. It can therefore be determined, whether the object has been completely influenced at least between the energy application part and the part of the safety margin sensed by the sensing part, without necessarily sensing the object between the position of the energy application part and the part of the safety margin sensed by the sensing part.

In an embodiment, the arrangement determination unit is adapted to determine the orientation of the energy application element also depending on the determined position of the energy application element. Thus, the orientation of the energy application element can be determined, while it is assumed that the position of the energy application part is fixed with respect to the object as determined by the arrangement determination unit.

In a preferred embodiment the arrangement determination unit is adapted to determine
  several positions of the energy application element by determining several positions of the energy application part and by determining several further energy application parameters, which correspond to the several positions of the energy application part, and
  several orientations of the energy application element for the several positions of the energy application element, such that
    the object representation is completely covered by several energy influence zones defined by the provided assignments, the several positions of the energy application part and the several further energy application parameters, and a provided safety margin surrounding the object representation is sensible by the sensing part. The several orientations of the energy application element can be determined such that the safety margin is sensible as homogenously as possible. This further improves the planning of the application of energy such that the object, which can be a tumor, is completely influenced by the energy, in particular, completely ablated, wherein at the same time the application of the energy can be reliably monitored by sensing the safety margin surrounding the object.

It is further preferred that the arrangement determination unit is adapted to determine a sequence of the several positions and orientations of the energy application element such that an energy influence zone generated by applying energy to the object in accordance with a determined first position, a determined first orientation, and a determined first energy application parameter, is sensible by the sensing part, while the energy application element is in a following determined second position and in a following determined second orientation. This allows assessing the result of applying energy to the object in accordance with a planned first position, a planned first orientation and a planned first energy application parameter by using the sensing part, while the energy application element is in the following planned second position and in the following planned second orientation. This allows the user to immediately react to the result of the application of energy in accordance with the first planned position, orientation and further energy application parameter. For example, if an undesired result is sensed, the second position, orientation and further energy application parameter and optionally further following positions, orientations and energy application parameters can consider this undesired result.

In a preferred embodiment, the object providing unit is adapted to indicate an impair region within or adjacent to the object, in which the application of energy is expected to be impaired, wherein the arrangement determination unit is adapted to determine the orientation of the energy application element such that the impair region is sensible by the sensing part. If the object is a part of a living being like a tumor, which should be ablated, the impair region can be a region close to a blood vessel, which may influence the application of energy due to heat drainage. The orientation of the sensing part is preferentially determined such that an impair region within a safety margin surrounding the object is sensible by the sensing part. The impair regions are regions, which are known to, for example, not behave as expected in accordance with an expected ablation zone. By arranging the energy application element that these impair regions are sensed, the influence of the energy can be sensed at these problematic regions and the planning of the energy application can consider the result of the sensing at these problematic regions, thereby allowing the energy application planning apparatus to further improve the quality of planning the application of energy.

It is preferred that the object providing unit is adapted to indicate a forbidden region within or around the object, in which the energy application element is not allowed to be located, wherein the arrangement determination unit is adapted to determine the orientation of the energy application element such that the energy application element is not located within the forbidden region. If the object is a part of a living being like a person or an animal, the forbidden region can be a bone region or a vessel region, which should not be damaged by the energy application element. This consideration of the forbidden region, while planning the application of energy, can further improve the quality of planning the application of energy.

It is further preferred that the energy planning application apparatus comprises a property determination unit for determining a property of at least one of the object and the surrounding of the object based on the generated sensing signal. If the energy application planning apparatus is adapted for planning an ablation procedure, the property determination unit is preferentially adapted to determine whether a sensed part of at least one of the object and of the surrounding of the object has been ablated based on the generated sensing signal.

In a preferred embodiment, the arrangement determination unit is adapted to amend the determined arrangement of the energy application element with respect to the object depending on the object representation and the determined property of at least one of the object and the surrounding of the object. Since the application of energy can be adapted to the already measured property of the object, in particular, based on whether regions of the object, which are expected to have been influenced by the energy already, are really already influenced by the application of energy, the planning of the application of energy can be further improved.

In a further aspect of the present invention an energy application apparatus for applying energy to an object is presented, wherein the energy application apparatus comprises:

an energy application element for applying energy to the object, the energy application element comprising an energy application part for applying energy to the object and a sensing part for generating a sensing signal being indicative of a property of at least one of the object and the surrounding of the object, an energy application planning apparatus for planning an application of energy as defined in claim 1.

The energy application apparatus allows therefore a user to or allows to automatically apply energy to the object in accordance with the energy application plan determined by the energy application planning apparatus. For example, the planned arrangement of the energy application element can be shown to the user on a display and the user can then arrange the energy application element in accordance with the determined planned arrangement. Alternatively, the energy application apparatus can comprise a steering unit for introducing the energy application element automatically into the object in the planned arrangement.

The energy application apparatus can comprise one or several energy application elements, in particular, one or several ablation needles. If the energy application apparatus comprises several energy application elements, energy can be applied and/or the object can be sensed at different positions simultaneously.

The sensing part can comprise an optical sensor for generating an optical sensing signal being indicative of the property of at least one of the object and the surrounding of the object. For example, at least one of the object and the surrounding of the object can be illuminated by light, wherein absorbed and scattered light can be collected by the optical sensor for generating the optical sensing signal. The optical sensing signal, which is indicative of the absorption and the scattering of the light, can be used by the property determination unit for determining the property of at least one of the object and the surrounding of the object, for example, for determining whether tissue has already been ablated.

The energy application element can comprise a further sensing part comprising a non-optical sensor. For example, the further sensing part can comprise a temperature sensor and/or a pressure sensor. The further sensing part can provide further information, which can be used for monitoring the application of energy to the object.

In a further aspect of the present invention an energy application planning method for planning an application of energy to an object is presented, wherein the energy application planning method comprises:

providing an object representation of the object by an object providing unit, providing an energy application element representation representing an energy application element including an energy application part for applying energy to the object and a sensing part for generating a sensing signal being indicative of a property of at least one of the object and the surrounding of the object by an energy application element providing unit, determining an arrangement of the energy application element with respect to the object depending on the positions of the energy application part and the sensing part with respect to the energy application element as defined by the energy application element representation and depending on the object representation by an arrangement determination unit.

In a further aspect of the present invention an energy application planning computer program for planning an application of energy to an object is presented, wherein the energy application planning computer program comprises program code means for causing an energy application planning apparatus as defined in claim 1 to carry out the steps of the energy application planning method as defined in claim 14, when the energy application computer program is run on a computer controlling the energy application apparatus.

It shall be understood that the energy application planning apparatus of claim 1, the energy application apparatus of claim 13, the energy application planning method of claim 14 and the energy application planning computer program of claim 15 have similar and/or identical preferred embodiments, in particular, as defined in the dependent claims.

It shall be understood that a preferred embodiment of the invention can also be any combination of the dependent claims with the respective independent claim.

These and other aspects of the invention will be apparent from and elucidated with reference to the embodiments described hereinafter.

DETAILED DESCRIPTION OF PREFERRED EMBODIMENTS

Figure 1:
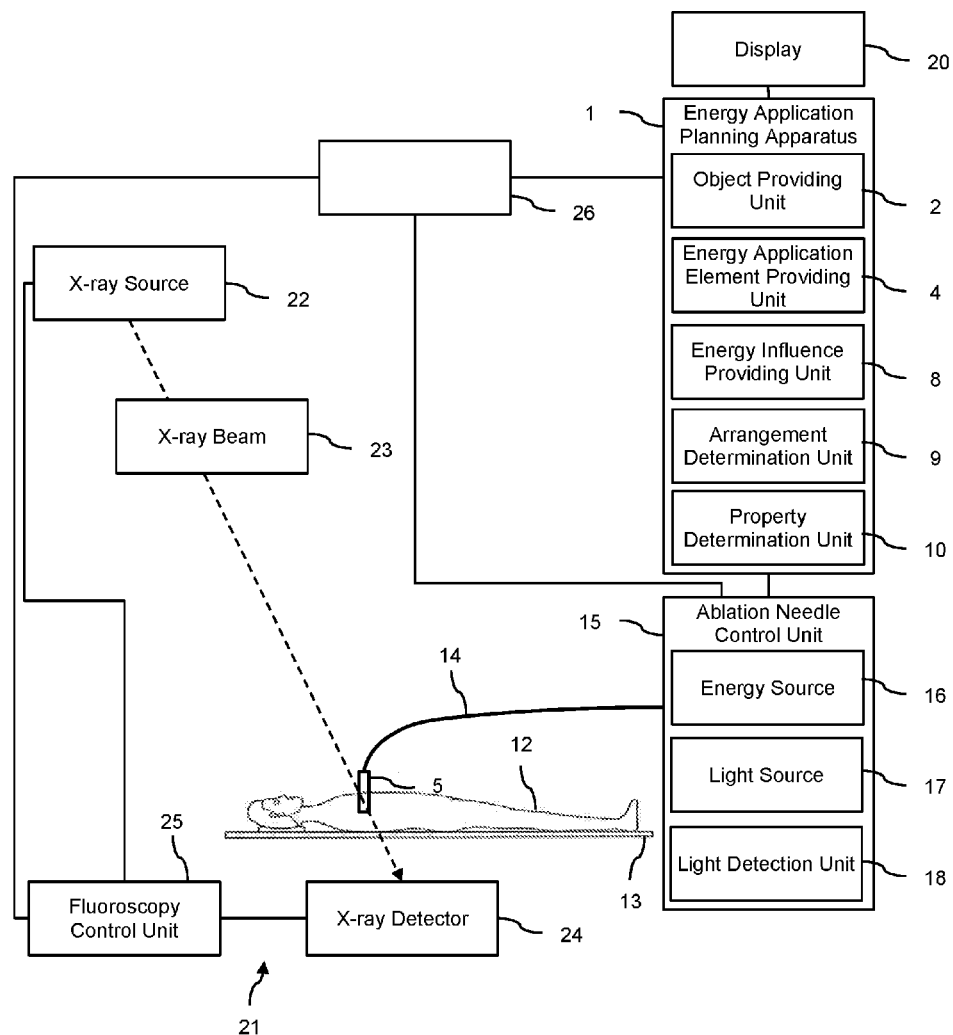
FIG. 1 shows schematically and exemplarily an embodiment of an energy application planning apparatus for planning an application of energy to an object.
Figure 2:
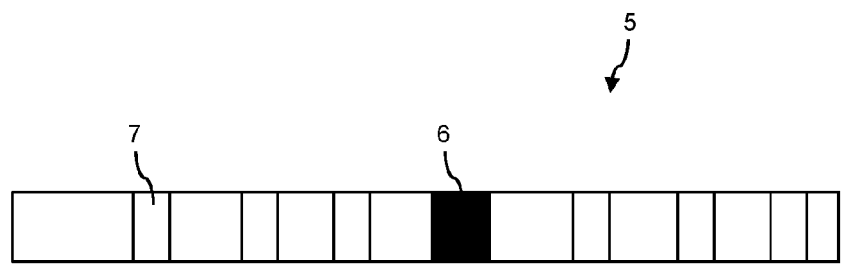
FIG. 2 shows schematically and exemplarily an embodiment of an ablation needle.

FIG. 1 shows schematically and exemplarily an embodiment of an energy application apparatus for applying energy to an object. The energy application apparatus 11 is an ablation apparatus for applying an ablation procedure to the object. The object is, in this embodiment, a tumor within a person 12 located on a table 13. The energy application apparatus 11 comprises an energy application element 5 for applying energy to the object. An embodiment of the energy application element 5 is schematically and exemplarily shown in more detail in FIG. 2.

The energy application element 5 is, in this embodiment, an ablation needle comprising an energy application part 6 for applying energy to the object and several sensing parts 7 for generating a sensing signal being indicative of a property of at least one of the object and the surrounding of the object. The energy application part 6 is surrounded by an equal number of sensing parts 7 on each side of the energy application part 6 on the energy application element 5. In this embodiment, three sensing parts 7 are provided on each side of the energy application part 6 on the ablation needle 5. In other embodiments, more or less sensing parts 7 can be provided on the energy application element 5.

In this embodiment, the sensing parts 7 comprise optical sensors for generating an optical sensing signal being indicative of a property of at least one of the object and the surrounding of the object. In particular, the optical sensors can comprise one or several optical fibers for emitting light, which is directed to the object, and one or several optical fibers for detecting light from the object for generating the optical signal. The optical sensing signal is preferentially indicative of the absorption and/or the scattering of the light and can be used for determining the property of at least one of the object and the surrounding of the object, for example, for determining whether tissue has already been ablated or not. The energy application part 6 preferentially comprises an ablation electrode being an RF ablation electrode. The sensing part 7 can be used for monitoring the development of an ablated region, while the ablation needle 5 is located within the tumor and while the ablation energy is applied by the ablation electrode.

The ablation needle 5 is connected to an ablation needle control unit 15 via a connection element 14 like a cable. The ablation needle control unit 15 comprises an electrical energy source 16, in particular, an RF source, for applying energy, in particular, RF energy to the object, via electrical connections within the connection element 14 and the ablation electrode. The ablation needle control unit 15 further comprises a light source 17, which provides light, which is guided to the sensing parts 7 of the ablation needle 5 by using one or several optical fibers, and a light detection unit 18 for detecting light, which has been altered by absorbance and/or scattering by the object, collected by one or several optical fibers and transferred to the light detection unit 18 by the one or several optical fibers. The ablation needle 5 can be guided and arranged by a user like a physician or radiologist under image guidance as will be described in the following.

During the guidance of the ablation needle 5 to the object and during the arranging procedure for arranging the ablation needle within the object in a desired position and in a desired orientation, a fluoroscopy device 21 images the ablation needle 5 within the person 12. The fluoroscopy device 21 comprises an X-ray source 22, which generates an X-ray beam 23 for traversing a region of the person 12, in which the ablation needle 5 is present. After the X-ray beam 23 has traversed the person 12, the X-ray beam 23 is detected by an X-ray detector 24. The X-ray source 22 and the X-ray detector 24 are controlled by a fluoroscopy control unit 25, which generates a fluoroscopy image based on the detected X-ray beam 23.

The energy application apparatus 11 further comprises an energy application planning apparatus 1 for planning the application of energy to the object. The energy application planning apparatus 1 comprises an object providing unit 2 for providing an object representation of the object, i.e., in this embodiment, a representation of a tumor to be ablated. The energy application planning apparatus 1 further comprises an energy application element providing unit 4 for providing an energy application element representation representing the energy application element 5, i.e., in this embodiment, the ablation needle 5, and an arrangement determination unit 9 for determining an arrangement of the energy application element 5 with respect to the object depending on the positions of the energy application part 6 and the sensing parts 7 with respect to the energy application element 5 as defined by the energy application element representation and depending on the object representation. In this embodiment, the arrangement determination unit 9 is adapted to determine several arrangements of the energy application element 5 with respect to the object for applying energy to the object several times.

The object providing unit 2 can be adapted to segment the object in a provided three-dimensional image of the person 12, which includes the object, like a computed tomography image or a magnetic resonance image for providing the object representation. Thus, the object representation is preferentially a three-dimensional segmented tumor. The object providing unit can also be a storing unit, in which the object representation, which has been determined already by another unit, is stored, or the object providing unit can also be an entire system comprising an imaging modality for generating a three-dimensional image showing the person 12 and the object with the person 12 and a segmentation unit for segmenting the object in the generated three-dimensional image.

The energy application element providing unit 4 is preferentially a storing unit, in which the energy application element representation is stored and from which the energy application element representation can be retrieved for determining the arrangement of the energy application element 5 with respect to the object. The energy application element providing unit 4 includes preferentially a model of the energy application element defining the positions of the energy application part and the sensing parts with respect to the energy application element 5, wherein the model is the energy application element representation.

The energy application planning apparatus 1 further comprises an energy influence assignment providing unit 8 for providing assignments between expected energy influence zones, which define an expected shape and an expected size of a zone of the object being influenced by the application of energy, and further energy application parameters. In this embodiment, the energy influence assignment providing unit 8 is adapted to provide assignments between expected ablation zones, which define the expected shape and the expected size of an ablated zone of the person 12, wherein within the ablated zone the tissue has been ablated, and further energy application parameters like the power of applying the RF energy, the time of applying the RF energy, et cetera.

The arrangement determination unit 9 can be adapted to determine the position of the energy application element 5 by determining the position of the energy application part 6 and a further energy application parameter depending on the object representation and the provided assignments. In particular, the arrangement determination unit 9 can be adapted to determine the position of the energy application element 5 by determining a position of the energy application part 6 and by determining a further energy application parameter such that the object representation is completely covered by the energy influence zone defined by the provided assignments, the position of the energy application part 6 and the further energy application parameter.

The arrangement determination unit 9 can be further adapted to determine the orientation of the energy application element 5 such that a provided safety margin surrounding the object representation is sensible by at least one of the sensing parts 7. The arrangement determination unit 9 can therefore not only determine the position of the energy application part 6 within the object, i.e., in this embodiment, within the tumor, but also the orientation of the energy application element 5 within the object as the arrangement of the energy application element 5. In particular, the arrangement determination unit 9 is preferentially adapted to determine several positions of the energy application element 5 by determining several positions of the energy application part 6 and by determining several further energy application parameters, which correspond to the several positions of the energy application part 6, and to determine several orientations of the energy application element 5 for the several positions of the energy application element 5 such that the object representation is completely covered by several energy influence zones defined by the provided assignments, the several positions of the energy application part 6 and the several further energy application parameters, and such that the provided safety margin surrounding the object representation is sensible by the sensing parts 7. In an embodiment, these arrangements of the energy application element 5 can be determined such that the safety margin is sensible as homogeneously as possible. Alternatively or in addition, the several orientations of the energy application element 5 can also be determined depending on other criteria.

For instance, the object providing unit 2 can be adapted to indicate an impair region within or adjacent to the object, in which the application of energy is expected to be impaired, wherein the arrangement determination unit 9 can be adapted to determine the orientation of the energy application element 5 such that the impair region is sensible by at least one of the sensing parts 7. The impair region can be a region close to a blood vessel, which may influence the application of energy due to heat drainage. A region close to a blood vessel can be determined, for example, by segmenting a blood vessel in a provided three-dimensional image of the person 12 including the object and the surrounding of the object. The same three-dimensional image may be used for determining the object representation, i.e., in this embodiment, the segmented tumor, and the impair region. The object providing unit can be adapted to indicate one or several impair regions, wherein the arrangement determination unit 9 can be adapted to orient the ablation needle 5 such that the one or several impair regions are sensible by the sensing parts 7. In an embodiment, the arrangement determination unit 9 is adapted to determine the orientations of the ablation needle 5 such that at least one or several impair regions within the provided safety margin are sensible by the sensing parts 7.

A further criterion, which may be used by the arrangement determination unit 9 for determining the orientation of the energy application element 5 can be a forbidden region within or around the object, in which the energy application element 5 is not allowed to be located. The object providing unit 2 can be adapted to indicate this forbidden region and the arrangement determination unit 9 can be adapted to determine the orientation of the energy application element 5 such that the energy application element 5 is not located within the forbidden region. The person 12 comprises regions, through which the ablation needle 5 cannot be navigated and in which the ablation needle 5 cannot be located. Such forbidden regions are defined, for example, by a bone region or a vessel region within the person 12, which should not be damaged by the ablation needle 5.

A further criterion, which can be used for determining the orientations of the energy application element 5, can be orienting the energy application element 5 such that an energy influence zone generated by applying energy to the object in accordance with a determined previous position, a determined previous orientation, and a determined previous energy application parameter, is sensible by the sensing parts 7, while the energy application element 5 is in a determined current position and a determined current orientation. Thus, a sequence of several positions and orientations of the energy application element 5 can be determined such that the sensing parts 7 in a current arrangement of the energy application element 5 can sense the energy influence zone generated, while the energy application element was arranged in a previous arrangement, in particular, in an immediately previous arrangement.

The energy planning application apparatus 1 further comprises a property determination unit 10 for determining a property of at least one of the object and the surrounding of the object based on the generated sensing signal. In particular, the property determination unit 10 is adapted to determine, whether a sensed part of at least one of the object and of the surrounding of the object has been ablated based on the generated sensing signal. This information regarding already ablated tissue can be used to amend already planned arrangements of the energy application element 5. For example, the object representation without the already ablated regions define a region to be ablated, wherein the arrangement determination unit 9 can be adapted to amend the following already planned arrangements of the energy application element by determining the positions of the energy application element for the following applications of energy such that the corresponding energy influence zones completely cover the region to be ablated.

The arrangement determination unit 9 can therefore be adapted to determine the positions of the energy application element 5 such that the object representation and/or the region to be ablated, which is defined by the object representation and already ablated regions, are completely covered by the energy influence zones and to determine the orientations of the energy application element 5 such that the safety margin, in particular, the safety margin in an impair region, is sensible by the sensing parts 7 and optionally further such that the energy application element is not located and navigated through a forbidden region and/or the sensing parts 7 can sense the result of a previous application of energy performed while the energy application element 5 was in previous arrangement.

The energy application apparatus 11 further comprises an apparatus control unit 26 for controlling the energy application planning apparatus 1, the ablation needle control unit 15 and the fluoroscopy device 21, and a display 20 for displaying, for example, a fluoroscopy image generated by the fluoroscopy device 21, an object representation, for example, a segmented three-dimensional tumor, an energy application element representation, et cetera.

Figure 3:
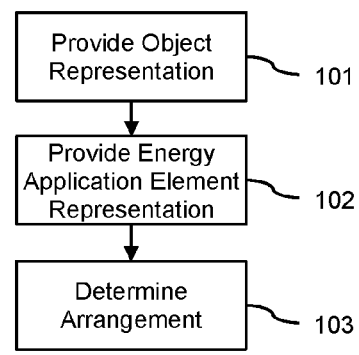
FIG. 3 shows a flowchart exemplarily illustrating an embodiment of an energy application planning method for planning an application of energy to an object.

In the following, an embodiment of an energy application planning method for planning an application of energy to an object will exemplarily be described with reference to a flowchart shown in FIG. 3.

In step 101, an object representation is provided by the object providing unit 2. In particular, a tumor is segmented in a three-dimensional image of the person 12, which comprises the tumor, and the segmented three-dimensional tumor is provided as the object representation. In step 102, an energy application element representation, which represents the energy application element 5 including the energy application part 6 and the sensing parts 7, is provided by the energy application element providing unit 4. In particular, a model of the ablation needle is provided, which defines the positions of the energy application part 6 and the sensing parts 7 on the ablation needle 5. In step 103, an arrangement of the energy application element 5 with respect to the object is determined depending on the positions of the energy application part 6 and the sensing parts 7 with respect to the energy application element 5 as defined by the energy application element representation and depending on the object representation by the arrangement determination unit 9. Preferentially, the arrangement determination unit 9 determines several positions of the energy application element 5 by determining several positions of the energy application part 6 and by determining several further energy application parameters like the power and the time of applying the energy, which correspond to the several positions of the energy application part 6, and several orientations of the energy application element 5 for the several positions of the energy application element 5 such that the object representation is completely covered by several energy influence zones defined by the provided assignments, the several positions of the energy application part 6 and the several further energy application parameters, and such that the provided safety margin surrounding the object representation is sensible by at least one of the sensing parts 7.

Figure 4:
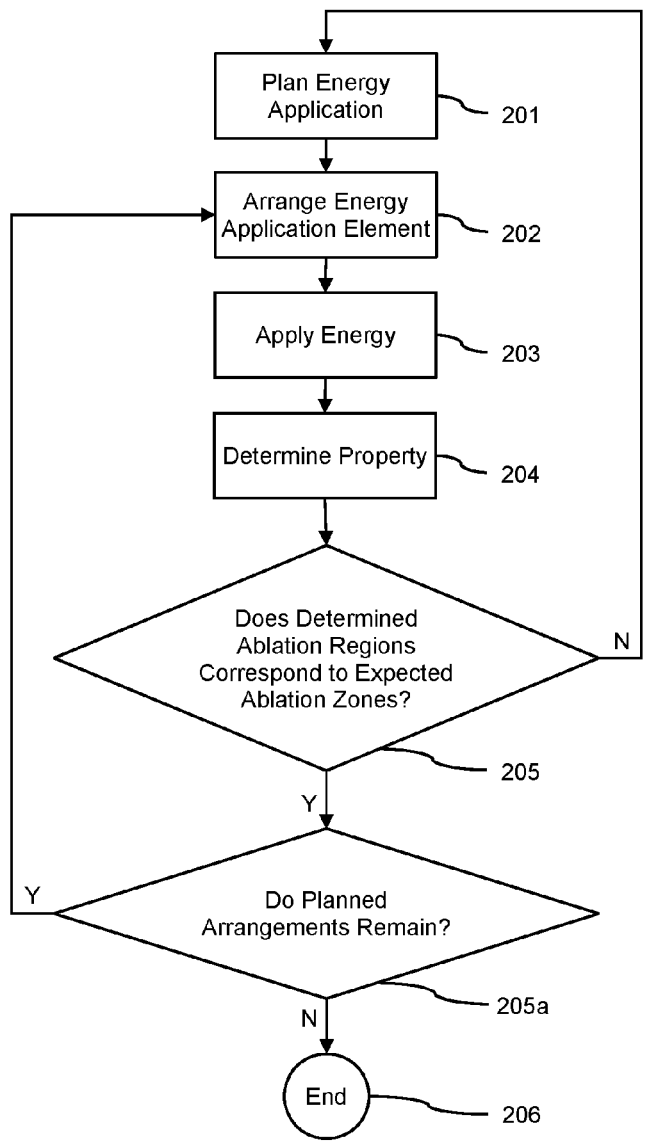
FIG. 4 shows a flowchart exemplarily illustrating an embodiment of an energy application method for applying energy to an object.

In the following, an embodiment of an energy application method for applying energy to an object will exemplarily be described with reference to a flowchart shown in FIG. 4.

In step 201, the application of energy is planned in accordance with the above described energy application planning method. In this embodiment, in step 201, several arrangements for arranging the energy application element 5 within the object are determined. In step 202, the energy application element 5 is arranged within the object in accordance with one of the determined several arrangements, and, in step 203, energy is applied to the object via the energy application part 6. Moreover, in step 203, the object and the surrounding of the object are monitored by using the sensing parts 7. In step 204, a property of at least one of the object and the surrounding of the object is determined based on sensing signals generated by the sensing parts 7 of the energy application element 5. In this embodiment, it is determined, whether the parts of at least one of the object and the surrounding of the object, which have been sensed by the sensing parts 7, have been ablated or not. In step 205, it is determined, whether the determined ablated regions correspond to an expected ablation zone, which was expected having regard to the position of the energy application part with respect to the object and having regard to the used energy application parameters like the used power settings and the time of applying energy to the object. If the determined ablated regions and the expected ablation zone are similar and if energy has not been applied in all arrangements of the energy application element 5 (Step 205a) determined in step 201, the energy application method continues with step 202. If the determined ablated regions deviate from the expected ablation zone, the already planned arrangements of the energy application element 5 are modified by planning these arrangements again under consideration of the determined already ablated regions. Thus, the method continues with step 201, in which a re-planning of the following arrangements is performed. If the determined ablated regions indicate that the object has been ablated completely (Step 205a), the energy application method ends in step 206.

In the field of oncology various tumors are treated with an ablation needle. Since the area that can be treated at one location of the ablation needle is limited, for larger sized tumors multiple ablations with different needle positions are required. In particular, planning of this ablation needle positioning is required for a good treatment of the tumor. Apart from planning, feedback on the ablation areas created at the different needle positions is helpful, because these areas can strongly depend on the tissue structure, i.e., for instance a blood vessel can act as a local heat sink and can reduce the size of the created ablation area. The energy application planning apparatus allows providing a feedback on the lesion growth, i.e., on the growth of the ablation zone, along the ablation needle direction and/or feedback on three-dimensional volume growth based on the sensed regions of at least one of the tumor and of the surrounding of the tumor sensed, while the ablation needle is located in different orientations. The energy application planning apparatus is adapted to not only plan the needle position by planning the position of the energy application part of the ablation needle, but to determine also the orientation of the ablation needle in such a way that the sensing part positions for the different ablation needle positions for the ablations sample the volume of the tumor ablation area in a representative way. The measurement information of these sensor part positions can be feedback to the planning algorithm. Depending on this feedback the treatment can be evaluated as being successful, and, if not successful, an additional ablation needle location can be planned, in order to ablate the tumor completely. The measurement information can be stored in the above mentioned three-dimensional image of the tumor and of the surrounding of the tumor, which has preferentially been used for segmenting the tumor, wherein the three-dimensional image with the stored measured optical feedback information can be shown in the display 20. For example, identified ablated and non-ablated regions can be colored differently on the display 20.

The energy application planning apparatus and the energy application apparatus can provide the advantage that, without additional needle insertion than those already needed for an ablation procedure, a representative inspection of the ablation zone can be obtained. Only a single ablation needle can be used, which is preferentially arranged several times in several positions and/or orientations for applying the ablation energy several times in different arrangements, or several ablation needles may be used during the ablation procedure so that the sensing parts of the several ablation needles can sense the tumor and/or the surrounding of the tumor at the same time. For example, two ablation needles can be arranged within the tumor such that the sensing parts of the two ablation needles can simultaneously sense the tumor and/or the surrounding of the tumor. The sensing parts preferentially comprise optical sensors. The ablation needle can further be equipped with other sensors, which are preferentially not located in the sensing parts, in which the optical sensors are located. These other sensors provide further information, which can be used for, for example, monitoring the growth of the ablation zone. These other sensors are, for instance, temperature sensors, pressure sensors, et cetera.

Figure 5:
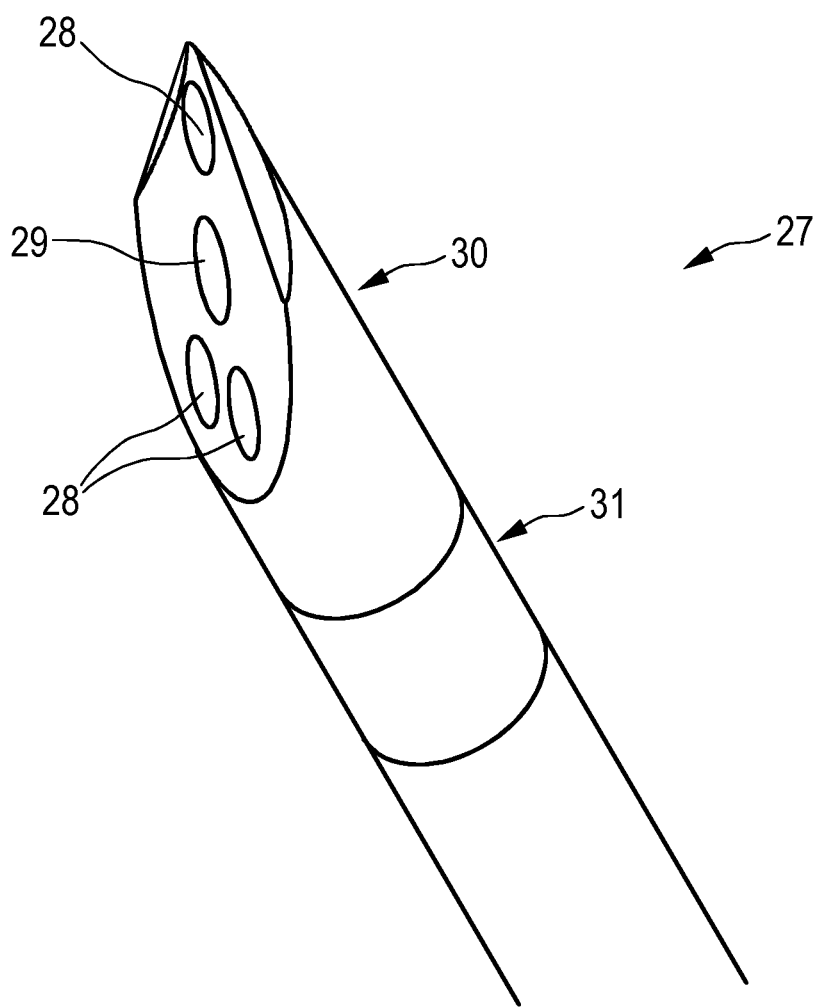
FIG. 5 shows schematically and exemplarily a tip of a further embodiment of an ablation needle.

FIG. 5 shows schematically and exemplarily a tip of a further embodiment of an ablation needle. The tip of the ablation needle 27 comprises optical fibers 28 and an irrigation hole 29. The end 30 of the tip of the ablation needle 27 comprises a metallic ablation electrode, which is separated from the further parts of the ablation needle 27 by an insulating bush 31. Within the tip of the ablation needle 27, in particular, within the metallic end 30 of the ablation needle 27, a temperature sensor like a thermal-couple can be situated for providing further information, which can be used, for instance, for monitoring the temperature during the ablation procedure and for providing the monitored temperature as a feedback to a user and/or to a controller for controlling the application of energy, in order to allow the user and/or the controller to apply the energy depending on the monitored temperature.

The optical fibers 28 form an optical sensor, wherein one or two of the optical fibers can emit light, which is absorbed and/or scattered by the tissue and wherein the other one or two optical fibers can collect the light being altered by absorbance and/or scattering by the tissue. The ablation needle 27 shown in FIG. 5 can comprise further sensing parts and/or energy application parts distributed along the ablation needle 27. Moreover, also the ablation needle 5 described above with reference to FIG. 2 can comprise a tip as shown in FIG. 5.

By using different needle positions and orientations, it is possible to probe the area around the tumor at different locations in the three-dimensional space allowing a representative probing of the ablation volume. Preferentially, the geometry of the tumor is known from a three-dimensional segmentation of the tumor in a provided three-dimensional image. The locations of the sensing part, in particular, of the RF ablation electrode, of the ablation needle can then be determined, wherein then the allowed angles of the ablation needle, i.e., possible orientations of the ablation needle, can be determined such that no vital structures like bones, vessels, et cetera are hit. From these possible angles, i.e., from these possible orientations, the angles of the ablation needle can be determined such that an optimal probing of the ablation zone is possible. Moreover, the order of the different arrangements, in which the ablation needle may be arranged, can be determined such that an ablated part of the tumor, which has been ablated, while the ablation needle was in a first orientation at a first location, can be probed, while the ablation needle is in a following second orientation at a following second position.

Figure 6:
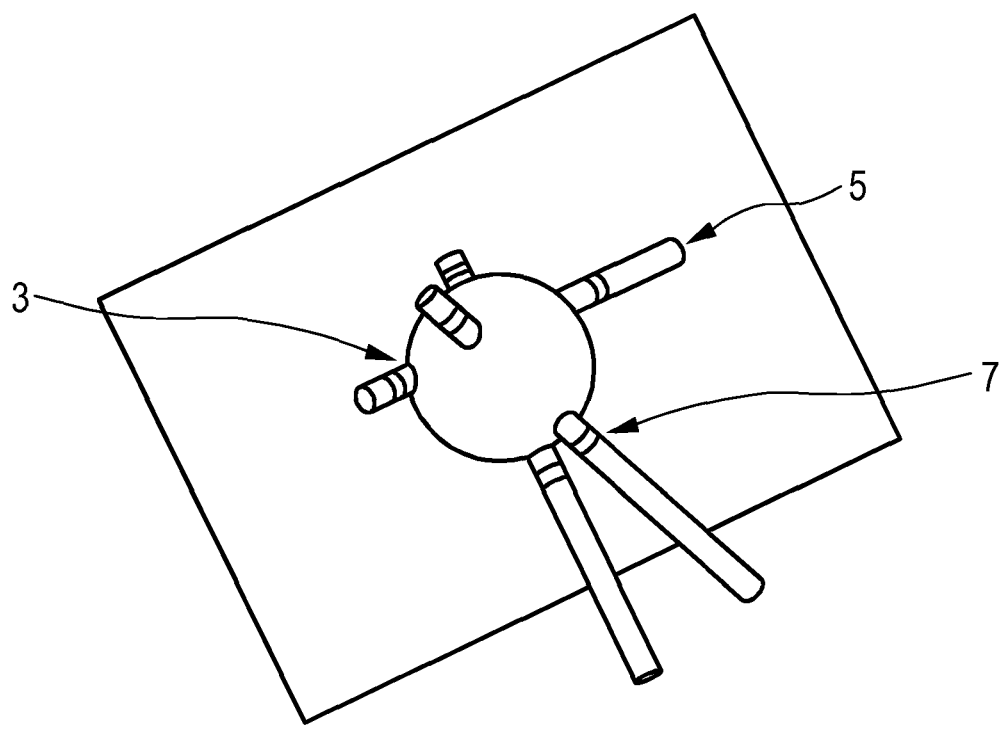
FIG. 6 shows schematically and exemplarily several arrangements of an ablation needle within an object.

FIG. 6 shows schematically and exemplarily three different arrangements of the ablation needle 5 within a tumor 3. The energy application part of the ablation needle 5 is within the tumor 3. In each arrangement of the ablation needle 5, two sensing parts 7 of the ablation needle 5 are located outside of the tumor 3 within a safety margin surrounding the tumor 3. The sensing parts 7 can therefore be used to determine whether the ablation zone has reached the safety margin.

The light source 17 can be a broadband light source like, for example, a tungsten halogen broadband lamp, or a laser, wherein the wavelength of the laser can be swept from, for example, 500 to 1600 nm. The sweeping can be performed by directly modifying the laser wavelength and/or by using, for example, an optical grating.

The light is transmitted to the sensing parts by using at least one optical fiber, wherein the transmitted light is emitted to the tissue, which absorbs and/or scatters the light, the light being altered by absorbance and/or scattering by the tissue is collected by at least one further optical fiber of the respective sensing part, and the collected light is transmitted to the light detection unit 18. The distal ends of an emitting fiber and of a collecting fiber are preferentially spatially separated by a distance of 1 to 3 mm, further preferred by a distance of 1 to 2 mm.

The intensity of the collected light is determined by the absorption and scattering properties of the object and/or of the surrounding of the object and can therefore be used for determining a property of the object and/or of the surrounding of the object. For example, it can be determined, whether the object and/or the surrounding of the object has been ablated or not. Upon spatial and temporal multiplexing, scattered and/or absorbed light can be collected at multiple sites of the ablation needle. Also a wavelength-dependent multiplexing can be performed.

Figure 7:
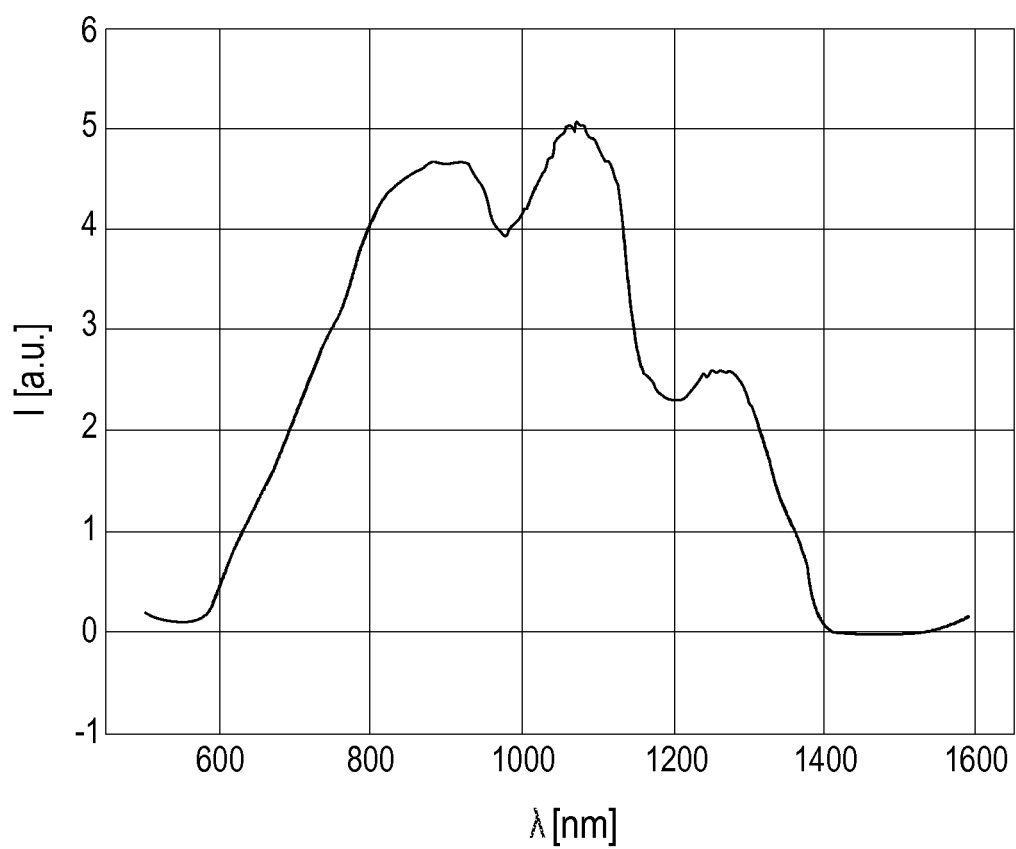
FIG. 7 shows exemplarily a reflectance spectrum of normal liver tissue.
Figure 8:
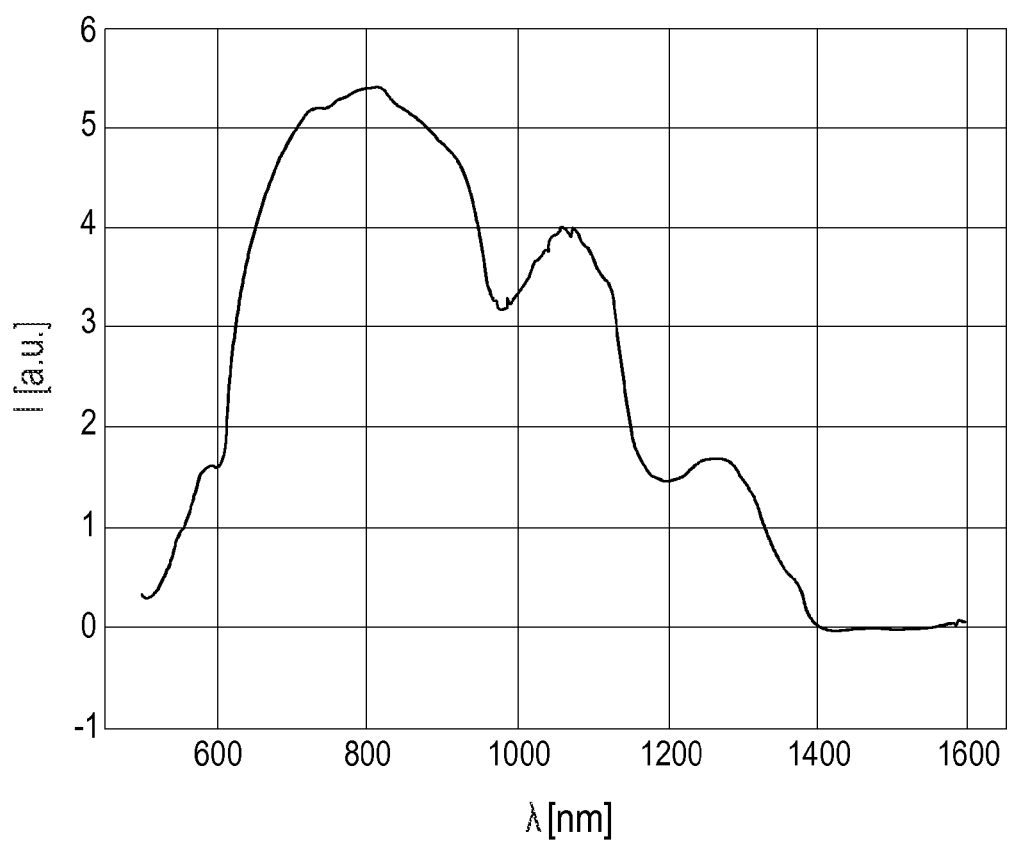
FIG. 8 shows exemplarily a reflectance spectrum of tumor liver tissue.
Figure 9:
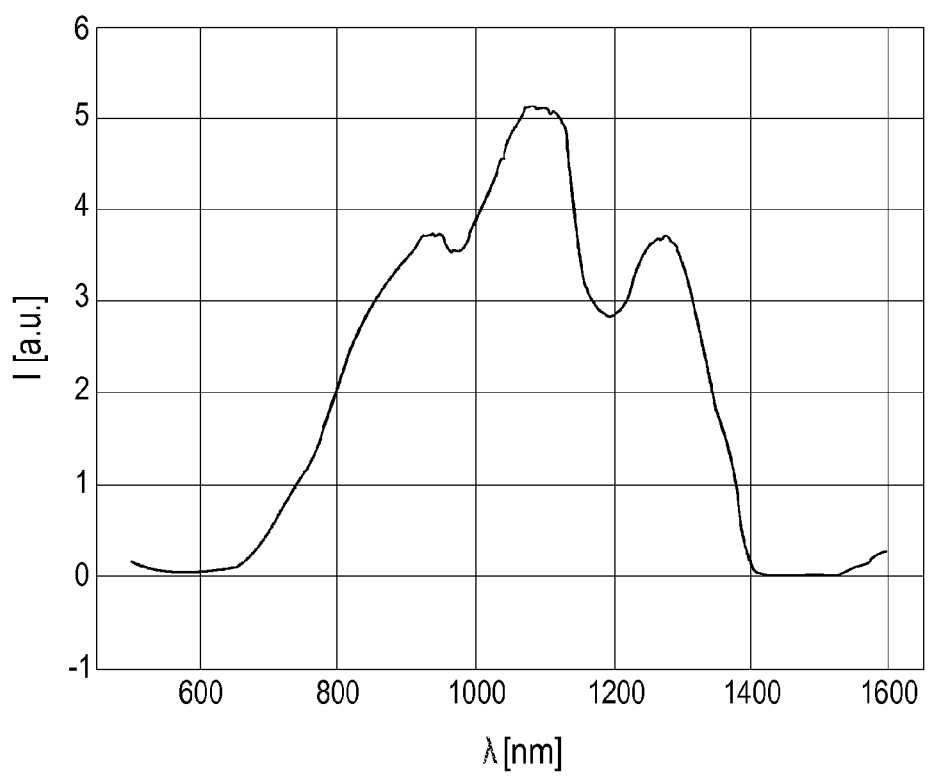
FIG. 9 shows exemplarily a reflectance spectrum of ablated liver tissue.

FIGS. 7 to 9 show exemplarily the measured spectra of different kinds of tissue. FIG. 7 shows a spectrum of normal liver tissue, FIG. 8 shows a spectrum of tumor liver tissue and FIG. 9 shows a spectrum of ablated liver tissue. As can be seen, these spectra are very different such that they can be used for distinguishing between normal liver tissue, tumor liver tissue and ablated liver tissue based on the collected absorbed and/or scattered light. FIGS. 7 to 9 show the intensity in arbitrary units depending on the wavelength in nm.

There are various ways to quantify the difference between the measured spectra as observed in FIGS. 7 to 9. For example, the property determination unit 10 can be adapted to compare an actually measured spectrum with known spectra of respective ablated tissue and respective non-ablated tissue and to determine whether the respective sensed part of the object is ablated or not based on the comparison. For the comparison a similarity measure like the sum of squared differences or a correlation of the spectra can be used.

Figure 10:
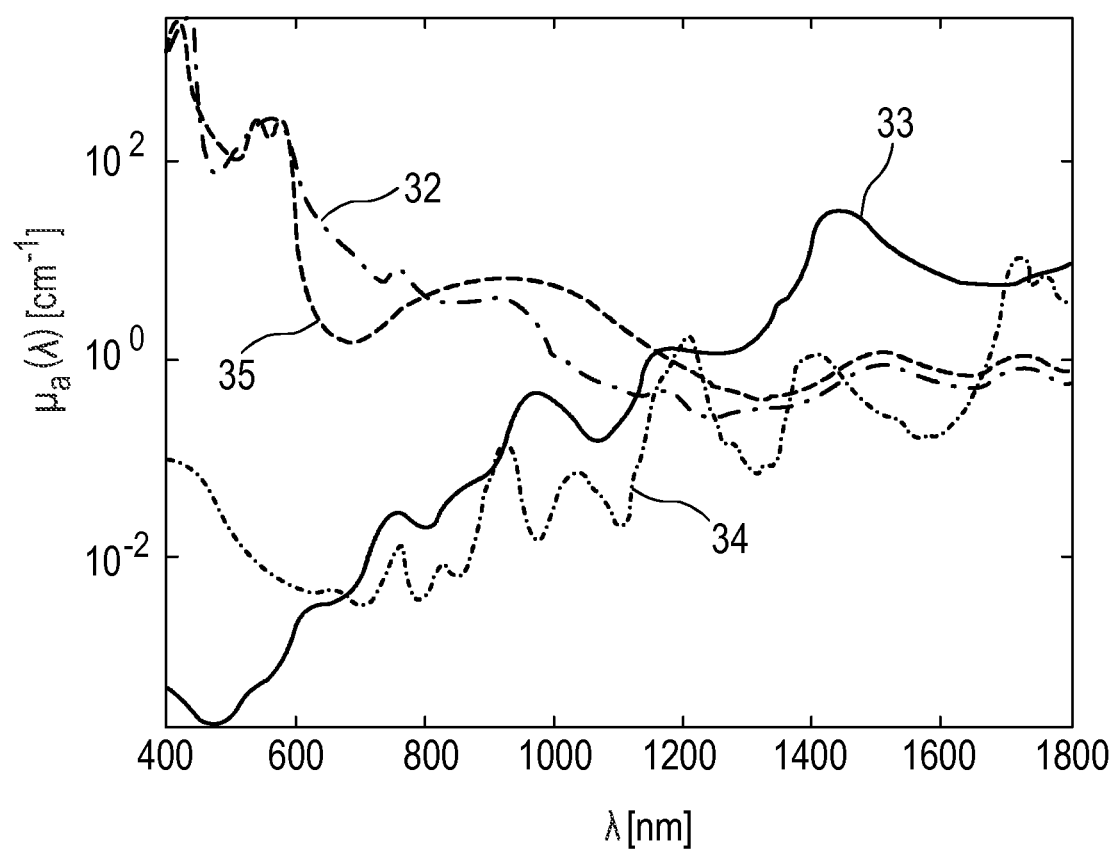
FIG. 10 shows exemplarily absorption spectra of oxygenated hemoglobin, hemoglobin, water and fat.

In an embodiment, optical tissue properties such as the scattering coefficient and the absorption coefficient of different tissue chromophores like hemoglobin, oxygenated hemoglobin, water, fat, et cetera are employed to quantify the difference between the spectra measured on non-ablated and ablated tissue. The chromophore concentrations can be determined by spectral fitting as described in the article "Estimation of lipid and water concentrations in scattering media with diffuse optical spectroscopy from 900 to 1600 nm" by Rami Nachabé et al., Journal of Biomedical Optics, 15 (3), 2010, which is herewith incorporated by reference, i.e. the spectral fitting disclosed in this article cannot only be applied to fat and water, but also to other elements like hemoglobin and oxygenated hemoglobin. The main absorbing constituents in normal tissue dominating the absorption in the visible and near-infrared range are blood (i.e. hemoglobin), water and fat. In FIG. 10 the absorption coefficients of these chromophores as a function of the wavelength are presented. In FIG. 10, the curve 35 denotes oxygenated hemoglobin, the curve 32 denotes hemoglobin, the curve 33 denotes water and the curve 34 denotes fat. Note that blood dominates the absorption in the visible range, while water and fat dominate in the near infrared range. These optical tissue properties change during tissue ablation and are significantly different for non-ablated tissue compared with ablated tissue. Furthermore, based on these properties different types of tissue, in particular, healthy muscle tissue, can be discriminated from already ablated tissue or from fat tissue.

The total absorption coefficient is a linear combination of the absorption coefficients of, for instance, blood, water and fat (hence for each component the value of that shown in FIG. 10 multiplied by its volume fraction). Correspondingly, the scattering coefficient can be expressed as a power law of the wavelength. By using the spectral fitting described in the above mentioned article by Nachabé et al. the volume fractions of the blood, water and fat as well as the scattering coefficients can be determined. With this method the measured spectra can be translated in physiological parameters that can be used to discriminate different tissues. In, for instance, the article by Nachabé et al. "Effect of bile absorption coefficients on the estimation of liver tissue optical properties and related complications in discriminating healthy and tumours samples", Biomedical Optics Express, vol. 2, pages 600 to 614 (2011), which is herewith incorporated by reference, the above method is used to discriminate, for example, healthy liver tissue from tumor liver tissue. Employing this method to the measured spectra shown in FIGS. 7 to 9 reveals that the water content as well the scattering increases in ablated tissue compared to non-ablated tissue. Furthermore, in this example the blood content in normal liver tissue is significantly higher than in tumor tissue. The property determination unit 10 can be adapted to determine whether tissue is ablated or non-ablated based on the above described spectral fitting procedure. For example, the property determination unit 10 can be adapted to determine the water content, the scattering coefficient, and the blood content by using the spectral fitting procedure, and to determine whether the tissue is ablated or non-ablated by comparing these measured tissue properties with corresponding stored tissue properties being indicative of ablated and non-ablated tissue.

Another way to discriminate differences in spectra is by making use of a principal components analysis. This method allows classification of differences in spectra and thus allows discrimination between tissues. It is also possible to extract features from certain parts of the spectra and use these to discriminate the various spectra. Moreover, changes in the water absorption spectra as a function of temperature can be used to determine the temperature of the tissue surrounding the needle.

Although diffuse reflectance spectroscopy is described above to extract tissue properties, also other optical methods can be used for determining a property of the object and/or of the surrounding of the object. For example, a fluorescence measurement, diffuse optical tomography by employing a plurality of optical fibers, differential pass length spectroscopy and/or Raman spectroscopy can be used for determining a property of the object and/or of the surrounding of the object.

The energy application planning apparatus and the energy application apparatus are preferentially adapted to be used in the field of oncology, in particular, for the planning of RF ablation treatments of tumors. However, the energy application apparatus and the energy application planning apparatus can also be used for ablating other objects like heart tissue for treating heart rhythm problems.

Although in the above described embodiments the sensing part of the energy application element comprises an optical sensor, in other embodiments the sensing part can also be adapted to use other techniques for sensing the object and/or the surrounding of the object. For instance, the object and/or the surrounding of the object can be sensed by using ultrasound or can be electrically sensed.

Although in the above described embodiments an ablation needle has been used for applying energy to the object, also other devices can be used for applying energy like a tip of an ablation catheter comprising an energy application element and at least one sensing element, wherein, in this case, the catheter tip does not comprise an ablation needle.

Although in the above described embodiments the energy application part comprises an RF electrode, the energy application part can also comprise another element for applying energy in another way. For example, the energy application part can be adapted to apply optical energy, for instance, for optically ablating tissue, or the energy application part can comprise an element for applying cold to the object, in particular, for performing a cyro-ablation.

Although in the above described embodiments the object, to which energy is applied, is a part of a living being, like a tumor or like cardiac tissue, in other embodiments the energy application apparatus can be adapted to apply the energy to a technical object.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Provisions like the provision of the object representation and the provision of the energy application element representation and determinations like the determination of the positions and orientations of the energy application element performed by one or several units or devices can be performed by any other number of units or devices. The provisions and determinations and/or the control of the energy application planning apparatus in accordance with the energy application planning method and/or the control of the energy application apparatus in accordance with the energy application method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. An energy application planning apparatus for planning an application of energy to an object, the energy application planning apparatus (1) comprising:
 an object providing unit (2) for providing an object representation of the object (3), an energy application element providing unit (4) for providing an energy application element representation representing an energy application element (5), the energy application element representation showing positions, with respect to the object representation, of an energy application part (6) for applying energy to the object (3) and of a sensing part (7) for generating an optical sensing signal being indicative of a property of at least one of the object (3) and the surrounding of the object (3), an arrangement determination unit (9) for determining an arrangement of the energy application element (5) with respect to the object (3) depending on the positions of the energy application part and the sensing part with respect to the energy application element as defined by the energy application element representation and depending on the object representation, wherein the arrangement determination unit (9) is adapted to determine the position and the orientation of the energy application element (5) with respect to the object (3) as the arrangement.

2. The energy application planning apparatus as defined in claim 1, wherein the energy application planning apparatus (1) comprises an energy influence assignment providing unit (8) for providing assignments between expected energy influence zones, which define an expected shape and an expected size of an area of the object being influenced by the application of energy, and wherein the arrangement determination unit (9) is adapted to determine the position of the energy application element by determining the position of the energy application part and to determine a further energy application parameter depending on the object representation and the provided assignments.

3. The energy application planning apparatus as defined in claim 1, wherein the arrangement determination unit (9) is adapted to determine the orientation of the energy application element such that a provided safety margin surrounding the object representation is sensible by the sensing part.

4. The energy application planning apparatus as defined in claim 2, wherein the arrangement determination unit (9) is adapted to determine several positions of the energy application element by determining several positions of the energy application part and by determining several further energy application parameters, which correspond to the several positions of the energy application part, and several orientations of the energy application element for the several positions of the energy application element, such that the object representation is completely covered by the expected energy influence zones defined by the provided assignments, the several positions of the energy application part and the several further energy application parameters, and a provided safety margin surrounding the object representation is sensible by the sensing part.

5. The energy application planning apparatus as defined in claim 4, wherein the arrangement determination unit (9) is adapted to determine a sequence of the several positions and orientations of the energy application element such that a first one of the expected energy influence zones generated by applying energy to the object in accordance with a determined first position, a determined first orientation, and a determined first energy application parameter, is sensible by the sensing part, while the energy application element is in a following determined second position and in a following determined second orientation.

6. The energy application planning apparatus as defined in claim 1, wherein the object providing unit (2) is adapted to indicate an impair region within or adjacent to the object, in which the application of energy is expected to be impaired, wherein the arrangement determination unit (9) is adapted to determine the orientation of the energy application element such that the impair region is sensible by the sensing part.

7. The energy application planning apparatus as defined in claim 1, wherein the object providing unit (2) is adapted to indicate a forbidden region within or around the object, in which the energy application element is not allowed to be located, wherein the arrangement determination unit (9) is adapted to determine the orientation of the energy application element such that the energy application element is not located within the forbidden region.

8. The energy application planning apparatus as defined in claim 1, wherein the energy planning application apparatus (1) comprises a property determination unit (10) for determining a property of at least one of the object and the surrounding of the object based on the generated optical sensing signal.

9. The energy application planning apparatus as defined in claim 8, wherein the energy application planning apparatus (1) is adapted for planning an ablation procedure and wherein the property determination unit (10) is adapted to determine whether a sensed part of at least one of the object and of the surrounding of the object has been ablated based on the generated optical sensing signal.

10. The energy application planning apparatus as defined in claim 8, wherein the arrangement determination unit (9) is adapted to amend the determined arrangement of the energy application element with respect to the object depending on the object representation and the determined property of at least one of the object and the surrounding of the object.

11. An energy application apparatus for applying energy to an object, the energy application apparatus (11) comprising:

an energy source (16) and an energy application element (5) for applying energy to the object (3), the energy application element comprising an energy application part (6) for applying energy to the object and a sensing part (7) for generating a sensing signal being indicative of a property of at least one of the object and the surrounding of the object, an energy application planning apparatus (1) for planning an application of energy as defined in claim 1.

12. An energy application planning method for planning an application of energy to an object, the energy application planning method comprising:

providing an object representation of the object by an object providing unit (2), providing an energy application element representation representing an energy application element, the energy application element representation including an energy application element, the energy application representation showing an energy sensing signal being indicative of a property of at least one of the object and the surrounding of the object by an energy application element providing unit (4), determining an arrangement of the energy application element with respect to the object depending on the positions of the energy application part and the sensing part with respect to the energy application element as defined by the energy application element representation and depending on the object representation by an arrangement determination unit (9), wherein the position and the orientation of the energy application element (5) with respect to the object (3) are determined as the arrangement.

13. An energy application planning program product for planning an application of energy to an object, the energy application planning program product comprises a non-transient computer readable medium having encoded thereon program code means for:

providing an object representation of the object by an object providing unit (2), providing an energy application element representation representing an energy application element, the energy application element representation showing an energy application part for applying energy to the object and a sensing part for generating an optical sensing signal being indicative of a property of at least one of the object and the surrounding of the object by an energy application element providing unit (4), determining an arrangement of the energy application element with respect to the object depending on the positions of the energy application part and the sensing part with respect to the energy application element as defined by the energy application element representation and depending on the object representation by an arrangement determination unit (9), wherein the position and the orientation of the energy application element (5) with respect to the object (3) are determined as the arrangement.

\* \* \* \* \*